United States Patent [19]
Bregen et al.

[11] Patent Number: 5,306,280
[45] Date of Patent: Apr. 26, 1994

[54] ENDOSCOPIC SUTURE CLIP APPLYING DEVICE WITH HEATER

[75] Inventors: Michael Bregen, Lebanon, N.J.; Brian H. Luscombe, Washington Crossing, Pa.

[73] Assignee: Ethicon, Inc., Somerville, N.J.

[21] Appl. No.: 926,099

[22] Filed: Aug. 5, 1992

Related U.S. Application Data

[62] Division of Ser. No. 844,253, Mar. 2, 1992, Pat. No. 5,171,251.

[51] Int. Cl.⁵ .............................. A61B 17/00
[52] U.S. Cl. .................. 606/143; 606/139; 606/142; 227/901
[58] Field of Search .............. 606/27–30, 606/40–42, 46, 49, 51, 52, 151, 142, 143, 139, 205–208; 227/901

[56] References Cited

U.S. PATENT DOCUMENTS

| | | | |
|---|---|---|---|
| 1,813,902 | 7/1931 | Bovie | 606/52 |
| 1,908,201 | 5/1933 | Welch et al. | 606/29 |
| 3,100,489 | 8/1963 | Bagley | 606/40 |
| 4,041,952 | 8/1977 | Morrison, Jr. et al. | 606/51 |
| 4,819,633 | 4/1989 | Bauer et al. | 606/52 |
| 4,936,842 | 6/1990 | D'Amelio et al. | 606/42 |
| 5,147,357 | 9/1992 | Rose et al. | 606/52 |
| 5,174,300 | 12/1992 | Bales et al. | 606/205 |
| 5,207,691 | 5/1993 | Nardella | 606/143 |
| 5,217,460 | 6/1993 | Knoepfler | 606/52 |

FOREIGN PATENT DOCUMENTS

| | | | |
|---|---|---|---|
| 2360298 | 6/1975 | Fed. Rep. of Germany | 606/29 |
| 235521 | 1/1978 | France | 606/52 |

Primary Examiner—Stephen C. Pellegrino
Assistant Examiner—Jeffrey A. Schmidt
Attorney, Agent, or Firm—Matthew S. Goodwin

[57] ABSTRACT

A method of clamping suture strand by applying heat and compressive force to a polymeric surgical clip having first and second opposed leg members so as to clamp the suture strand between the opposed inner clamping surfaces of the first and second leg members; a surgical clip defined by first and second leg members, the first leg member having a hole therein; and a surgical device for clamping a clip about a suture, such device defined by a trigger-activated handle, clamping jaws with a heating element disposed on one of the clamping members of the clamping jaws, a shaft connecting the jaws to the handle, and means for activating the heating element and for delivering compressive force to the clamping jaws to close the clip about a suture.

9 Claims, 3 Drawing Sheets

ENDOSCOPIC SUTURE CLIP APPLYING DEVICE WITH HEATER

This is a division of application Ser. No. 844,253, filed Mar. 2, 1992, now U.S. Pat. No. 5,171,251, which is hereby incorporated by reference.

BACKGROUND OF THE INVENTION

This invention relates generally to a surgical clip. More particularly, it relates to such a clip suitably adapted to replace a suture knot during endoscopic surgery, as well as a method of applying such a clip to clamp a suture, and a device for accomplishing this method.

As medical and hospital costs continue to increase, surgeons are constantly striving to develop advanced surgical techniques. Advances in the surgical field are often related to the development of operative techniques which involve less invasive surgical procedures and reduce overall patient trauma. In this manner, the length of hospital stays can be significantly reduced, and therefore the hospital and medical costs can be reduced as well.

One of the truly great advances in recent years to reduce the invasiveness of surgical procedures is endoscopic surgery. Endoscopic surgery involves the use of an endoscope, which is an instrument permitting the visual inspection and magnification of any cavity of the body. The endoscope is inserted through a cannula after puncture through the wall of the body cavity with a trocar, which is a sharp-pointed instrument. The surgeon can then perform diagnostic and therapeutic procedures at the surgical site with the aid of specialized instrumentation designed to fit through additional cannulas providing small diameter openings into the desired body cavity as may be required.

An age-old procedure which surgeons are required to perform to repair or reconstruct traumatized bodily tissue is suturing. Fortunately, medical instruments have been recently designed to allow a surgeon to manipulate a suture, or suture and needle combination, through the small diameter opening of a cannula. However, the ability to tie an appropriately placed suture knot has become troublesome and problematical.

Therefore, in response to this problem, surgeons have sought alternatives to conventional knot-tying techniques which would be suitable during endoscopic surgery. Among these alternatives include the use of hemostatic clips, which are designed to ligate blood vessels and other tubular members, to replace suture knots. Such hemostatic clips are described, for example, in U.S. Pat. Nos. 4,418,694 and 4,476,865. These clips can be readily applied with a clip applier which is designed to function through the small opening of a cannula. Unfortunately, the force required to displace these clips from the suture is inadequately low. As a result, hemostatic clips of the type shown in the art are unsuitable for general endoscopic surgery needs.

More recently, attempts have been made specifically to replace tying suture knots. U.S. Pat. 4,662,068 describes an apparatus which performs the multiple functions of fusing adjacent suture strands together as well as cutting the strands after the fusing operation is performed. Unfortunately, such a device is unable to transmit to the adjacent suture strands an adequate adhesive force to prevent the suture strands from disengaging. U.S. Pat. No. 4,078,731 describes a suture clip which eliminates the need for tying suture knots. The clip is configured in such a manner which allows the clip to be manipulated into a first position which defines a complete passageway around the suture being threaded through the clip. Once the clip is placed adjacent to desired bodily tissue, the clip is manipulated into a second position for clamping the suture. Although this clip can be designed to achieve adequate clamping force, unfortunately the overall design of the clip requires delicate fabrication which can lead to practical difficulties.

In view of the deficiencies of the prior art for creating a useful alternative to tying a suture knot, what is desired within the medical community is a clip and a method for applying the clip using endoscopic techniques which can successfully replace the suture knot. In addition it would be helpful if a suitable clip applier were developed which could be used in conjunction with such a clip and the method for applying the clip.

BRIEF DESCRIPTION OF THE DRAWINGS

The present invention will be described in greater detail in conjunction with the accompanying drawings wherein.

SUMMARY OF THE INVENTION

Figure 1:
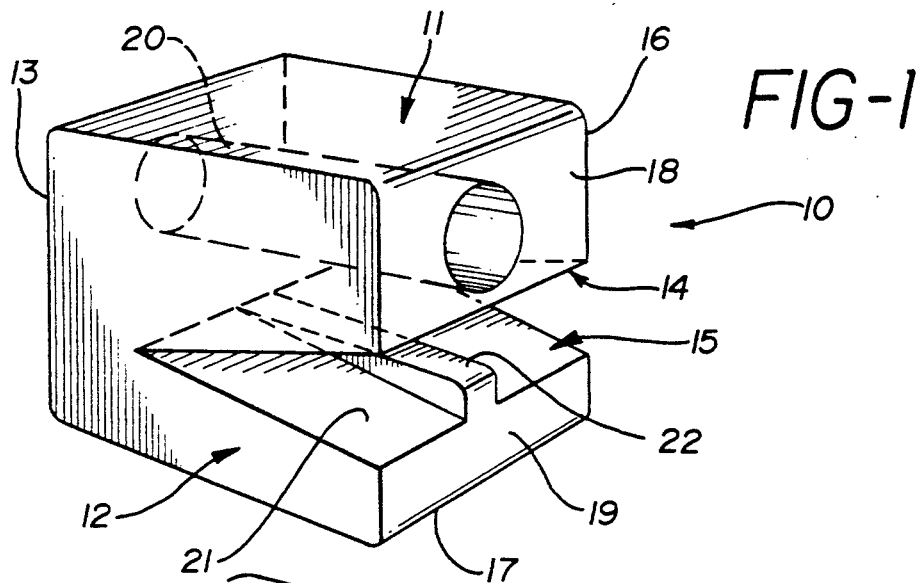
FIG. 1 is a perspective view of the surgical clip of the present invention.

In one aspect, the invention is a method of securely anchoring a strand of suture without tying a surgical knot. The method comprises the steps of a) providing a surgical clip composed of a polymeric material with first and second leg members joined at their proximal ends, each leg member having a clamping inner surface, said clamping inner surface being in opposition to the clamping inner surface of the other leg member; b) placing the strand of suture between the clamping inner surfaces of the first and second leg members; c) applying heat to at least a portion of the clip so as to soften the polymeric material from which the clip is composed; d) applying compressive force against the first and second leg members of the clip while the clip is in a softened state so as to clamp the strand of suture between the clamping inner surfaces of the first and second leg members; and e) removing the heat and compressive force from the clip.

In another aspect, the invention is a surgical clip. The surgical clip comprises first and second leg members. Each leg member has an outer grasping surface, a clamping inner surface, and an outer distal surface connecting the outer grasping to the clamping inner surface. The clamping inner surface of each leg member is in opposition to the clamping inner surface of the other leg member. In addition, the first leg member has a hole therein.

In a further aspect of the invention, the invention is a surgical device for clamping a surgical clip about a suture, in which the clip is composed of a polymeric material with first and second opposed leg members. The device comprises a) a handle having a base and an actuating trigger movably attached to the base, b) clamping jaws having first and second opposed clamping members configured to grasp the first and second opposed leg members of the clip, c) a heating element disposed on the first clamping member, d) a tubular shaft for connecting the handle to the clamping jaws, e) first means for activating the heating element such that when the clip is grasped in the clamping jaws and the heating element is activated, the polymeric material from which the clip is composed softens, and f) second means for delivering compressive force to the first and second opposed clamping members of the clamping jaws so as to close the first and second opposed leg members of the clip about the suture when the polymeric material from which the clip is composed is softened.

The method of this invention provides a unique way of using a simple clip design to securely anchor or fasten a strand of suture with an adequate clamping force and adhesive power to prevent the suture strand from disengaging. Surprisingly, the clamping and adhesive forces are adequate to eliminate the need for tying suture knots. Advantageously, the method of this invention is used in conjunction with endoscopic surgery, and therefore represents a tremendous advance in the state of the medical art by eliminating the need for tying suture knots.

A surgical clip of the invention is simple in design, easy to fabricate, and can be used with a vast array of surgical devices for applying the clip. The device of this invention for applying the clip can be especially adapted for use during endoscopic procedures which require the manipulation and placement of the clip within the body cavity through a trocar.

The invention as described herein can be utilized in any surgical procedure which requires suturing, and therefore requires the fastening or anchoring of a suture strand.

DESCRIPTION OF THE PREFERRED EMBODIMENTS

Referring to FIG. 1, there is shown a surgical clip 10 of the present invention. The surgical clip has a first leg member 11 and a second leg member 12 which join together at their proximal ends at outer proximal surface 13. The first leg member has a clamping inner surface 14, an outer grasping surface 16, and an outer distal surface 18 which facially connects the clamping inner surface to the outer grasping surface. Correspondingly, the second leg member has a clamping inner surface 15, an outer grasping surface 17, and an outer distal surface 19 which connects the outer grasping surface to the clamping inner surface. The clamping inner surface of the first leg member is a substantially flat surface, while the opposed clamping inner surface of the second leg member has a major surface 21 which is substantially flat and a ridge 22 formed on this major surface. The ridge extends longitudinally from the outer distal surface of the second leg member in a direction substantially parallel to the axis of the second leg member. The ridge facilitates the clamping force which is placed upon a suture strand when the strand is clamped within the clip.

The clip has a hole 20 extending therethrough for facilitating the application of heat internally to the clip to allow the material from which the clip is composed to achieve a softened state for clamping. Alternatively, the hole can be used to allow placement of the clip on the shaft of a clip applier, while heat is applied to another portion of the clip from a source located on the clamping jaws of the clip applier. The hole is advantageously disposed within the first leg member between the outer grasping surface and the clamping inner surface. The hole is desirably cylindrical for ease of fabrication, and extends completely through the first leg member from the outer distal surface 18 to the outer proximal surface 13. For ease of manipulation of the clip when a heating element is inserted into the hole, the hole is advantageously disposed in a direction which is substantially parallel to the axis of the first leg member.

The surgical clip of this invention can be made of any polymeric material which is biocompatible with bodily tissue and bioabsorbable. The preferred bioabsorbable polymeric materials are homopolymers and copolymers of glycolide, lactide, para-dioxanone, trimethylene carbonate and $\epsilon$-caprolactone. The preferred polymer material is derived from the polymerization of para-dioxanone, because of the low softening temperature of polymers derived from para-dioxanone.

The preferred means for fabricating the clip from bioabsorbable polymeric materials is to inject a suitable polymer melt into an appropriately designed mold at process conditions conventionally employed for such polymer systems. After the polymer melt cools in the mold, polymer shaped in the proper configuration to meet the design criteria of the clip is released from the mold. The molded clip can then be sterilized using conventional methods to render the clip suitable for surgical applications.

Figure 2:
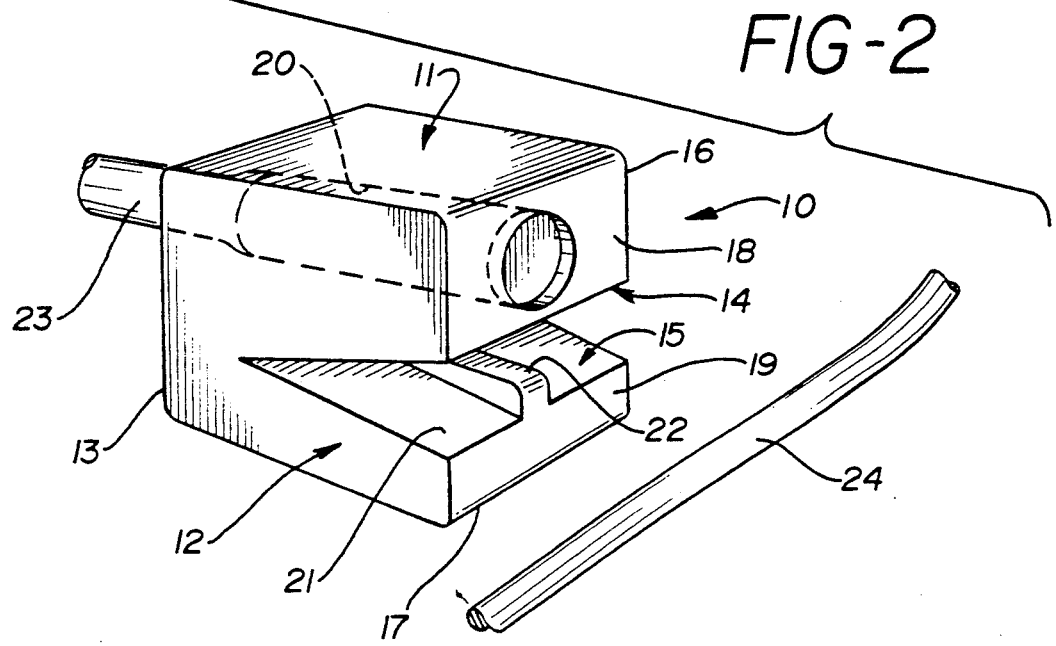
FIG. 2 is a perspective view of the surgical clip and a suture strands prior to clamping the suture strands.
Figure 3:
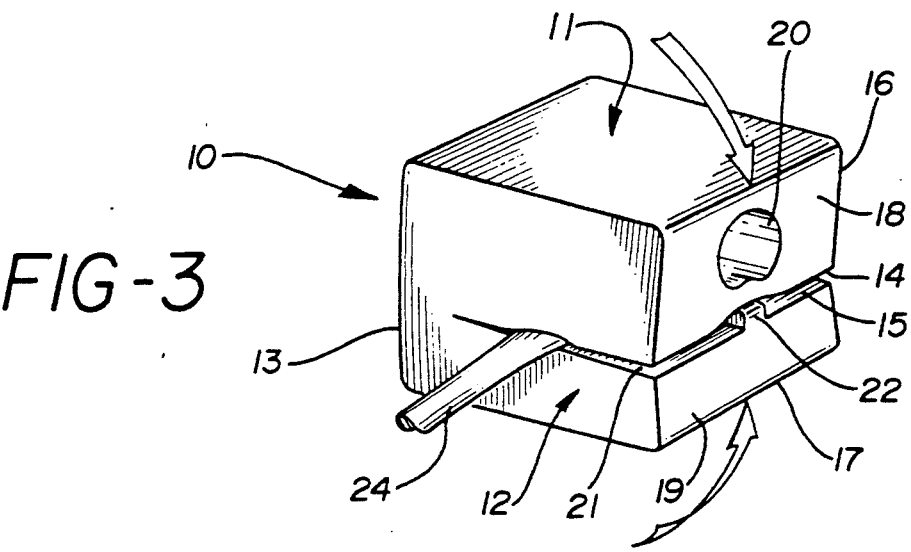
FIG. 3 is a perspective view of the clip of FIG. 2 after the clip is clamped about the suture strands.

Referring now to FIGS. 2 and 3, there is shown the process by which the clip of this invention can be clamped about a strand of suture 24, thus eliminating the need to tie a surgical knot during surgery. A heating element 23 can be extended through the first leg member of the clip. Once the heating element is extended through the clip, and the clip is ready to be softened, the suture strand which is desired to be clamped is placed between the clamping inner surfaces of the leg members of the clip. When the suture strand is properly positioned between the opposed inner surfaces, the heating element can be activated so that heat generated from the heating element raises the temperature of the polymeric material from which the clip is composed until such temperature exceeds the softening temperature of the polymeric material. This temperature is most often achieved when the temperature of the polymer exceeds its glass transition temperature. When the proper softening temperature is reached, compressive force can be applied to the opposed leg members as shown by the direction of the arrows at FIG. 3, so that the suture strand becomes securely clamped between the clamping inner surfaces of the leg members of the clip. When the clamping operation is completed, the heat and the compressive force can then be removed.

Advantageously, this method can be used to fasten or anchor not only one strand of suture but also two or more adjacent strands of suture. This can be accomplished because of the high pull force required to disengage the clamped strands due to the combination of clamping and adhesive action of the clip.

The method of the invention is advantageously carried out over a very short period of time, preferably within less than 10 seconds. This can be accomplished by applying a short burst of heat energy to the leg member, while simultaneously applying compressive force to the leg members to clamp the suture within the inner surfaces of the clip. Although this would be the preferred means for carrying out the invention, it is certainly not a limiting factor in how the method of the invention can be carried out.

Figure 5:
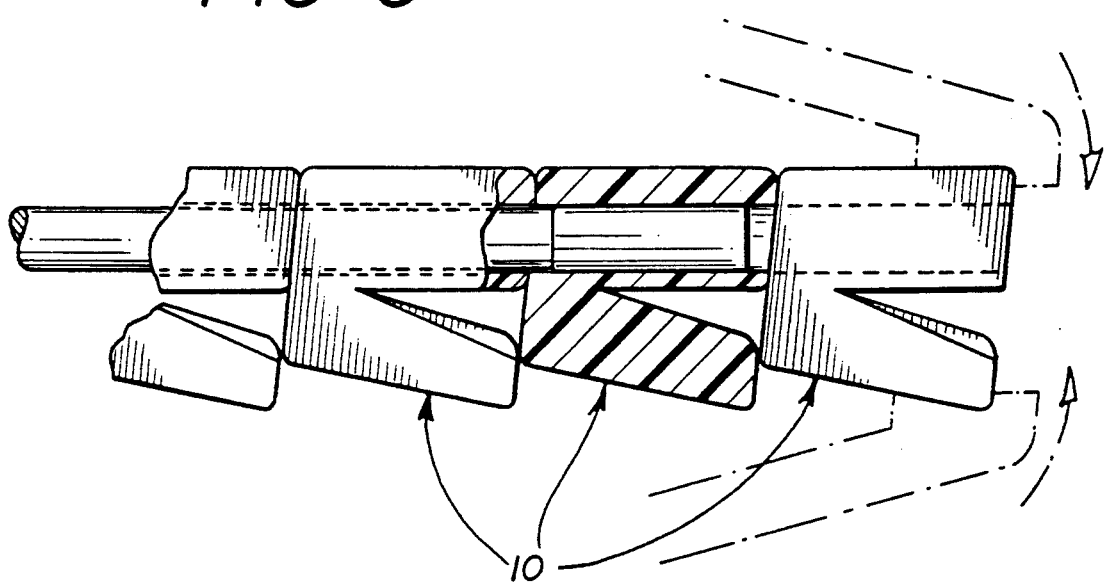
FIG. 5 is an enlarged detail view of a plurality of clips of this invention used in conjunction with a device for applying multiple clips.

An alternative embodiment of the invention is illustrated at FIG. 5. A shaft of a device for grasping a clip and applying compressive force is designed to carry a plurality of clips on the shaft for proper placement within the body. A heating element can be placed on the longitudinal shaft at its distal tip or alternatively, on the grasping member of the device. Heat is then applied to at least a portion of the most distally disposed clip on the shaft to soften the clip, and the softened clip is pushed distally from the shaft to fully engage the grasping member of the device. The grasping member of the device can then be activated to apply compressive force on the clip for clamping about a suture. In turn, the remaining clips would be pushed distally along the shaft for continuing application of multiple clips.

Figure 6:
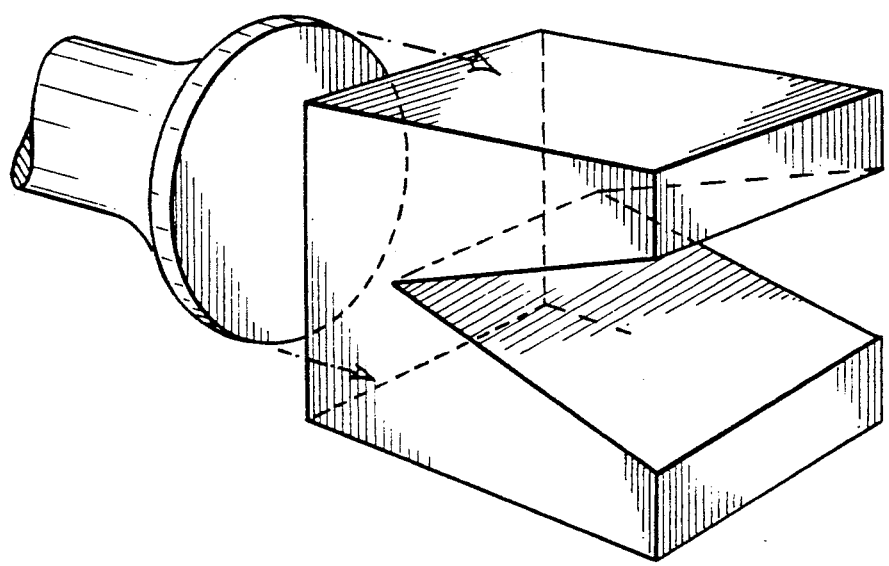
FIG. 6 is a perspective view which illustrates another embodiment for using the method of this invention with a conventional clip to attach adjacent suture strands.

FIG. 6 illustrates that it is unnecessary to utilize a clip having a hole extending through one of its leg members to practice the method of this invention. It is entirely possible to use a heating element which can be attached or contacted in some fashion to any clip having two opposed leg members, provided at least a portion of such a clip can be heated to a temperature above its softening temperature for subsequent application of compressive force on the leg members for clamping.

Figure 4:
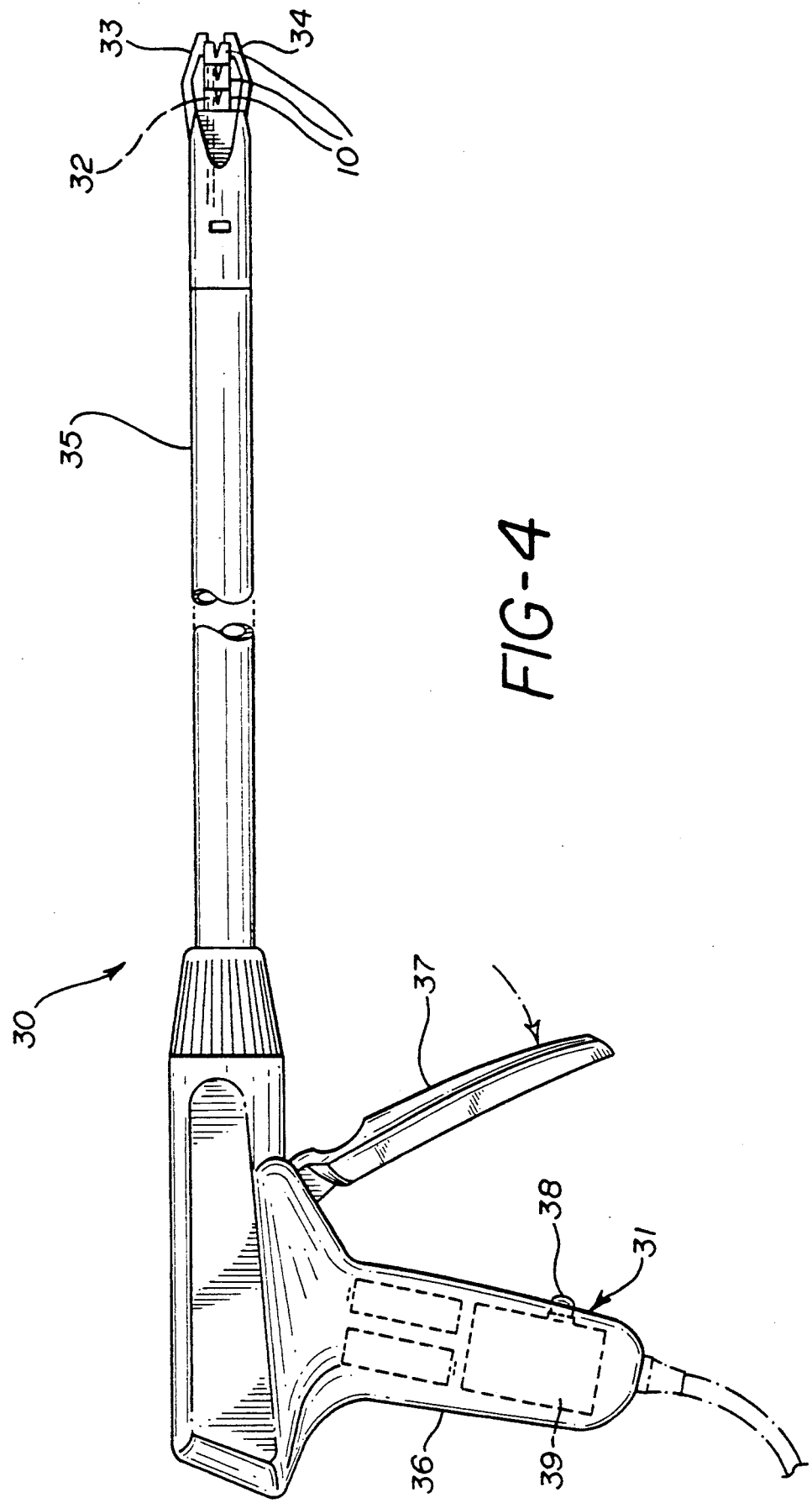
FIG. 4 is a side elevational view of a device that can be used for applying the clip.

FIG. 4 shows a surgical device 30 of this invention for clamping surgical clip 10. The device as shown can be utilized with the alternative embodiment depicted in FIG. 5 for the application of multiple clips. The device includes a trigger-activated handle 31 having a base 36 and an actuating trigger 37. The trigger can be squeezed against the base when the user applies force in the direction of the arrow as shown. After the application of such force, the trigger returns to its position shown in FIG. 4. In addition to the handle, there is a longitudinal tubular shaft 35 which connects the handle to clamping jaws 32. The longitudinal shaft has a long neck which is suitably configured to be placed down a trocar sleeve during endoscopic surgery. The clamping jaws have first and second opposed clamping members, shown at 33 and 34 respectively, configured to grasp the first and second opposed leg members of a clip. The first clamping leg member has a heating element 32 disposed thereon for applying heat to the most distally-positioned clip. Alternatively, the heating element could be disposed at the distal end of the shaft, where it can extend through the hole of the most distally-positioned clip.

To use the surgical instrument shown in FIG. 4, the user would squeeze the trigger against the base of the handle to activate contact switch 38, which in turn would power a suitable power source 39. This power source may be a low voltage battery which also may be rechargeable. Once the battery is turned on, the heating element is activated and the clip is softened while grasped within the clamping jaws of the instrument. Simultaneously with this action, the squeezing of the trigger causes the clamping jaws of the instrument to apply compressive force against the leg members of the clip for clamping the clip about a suture.

While this invention has been described in its most preferred embodiments, there are a vast array of additional embodiments which would fall within the scope of the claimed invention as defined by the appended claims, and such additional embodiments should not be construed to fall outside the scope of the appended claims merely because they have not been specifically described herein.

We claim:

1. A surgical clip applying device comprising:
   a) a handle having a base and an actuating trigger movably attached to said base,
   b) clamping jaws having first and second opposed clamping members, said first clamping member having a first grasping means and said second clamping member having a second grasping means wherein the first and second grasping means are configured on the opposing clamping members to grasp the outer surfaces of a surgical clip when compressive force is applied to the surgical clip via the clamping jaws,
   c) a tubular shaft for connecting said handle to said clamping jaws,
   d) a longitudinal shaft connected to said handle and positioned between said clamping jaws for retaining one or more surgical clips,
   e) a heating element incorporated in the distal end of the longitudinal shaft for heating a surgical clip,
   f) a first means for activating said heating element,
   g) a second means for delivering compressive force to said first and second opposed clamping members of said clamping jaws.

2. The surgical clip applying device of claim 1 wherein said base of said handle has a contact switch disposed on the surface thereof.

3. The surgical clip applying device of claim 2 wherein said first and second means are activated by squeezing said trigger of said handle so as to cause contact between said trigger and said contact switch thereby activating said switch.

4. In combination a surgical clip applying device and a surgical clip for use therewith comprising:
   a) a surgical clip having a first and second leg members, each leg member having an outer grasping surface, a clamping inner surface, and an outer distal surface connecting said outer grasping surface to said clamping inner surface, said clamping inner surface being in opposition to the clamping inner surface of the other leg member, said first leg member having a hole therein,
   b) handle having a base and an actuating trigger movably attached to said base,
   c) clamping jaws having first and second opposed clamping members, said first clamping member having a first grasping means and said second clamping member having a second grasping means wherein the first and second grasping means are configured on the opposing clamping members to grasp the outer surfaces of a surgical clip when compressive force is applied to the surgical clip via the clamping jaws,
   d) a tubular shaft for connecting said handle to said clamping jaws,
   e) a longitudinal shaft connected to said handle and positioned between said clamping jaws retaining one or more surgical clips,
   f) a heating element incorporated in the distal end of the longitudinal shaft for heating a surgical clip, g) a first means for activating said heating element, h) a second means for delivering compressive force to said first and second opposed clamping members of said clamping jaws.

5. The surgical clip applying device of claim 2 wherein said base of said handle has a contact switch disposed on the surface thereof.

6. The surgical clip applying device of claim 2 wherein said first and second means are activated by squeezing said trigger of said handle so as to cause contact between said trigger and said contact switch thereby activating said switch.

7. In combination a surgical clip applying device and a surgical clip for use therewith comprising:
a) a surgical clip having a first and second leg members, each leg member having an outer grasping surface, a clamping inner surface, and an outer distal surface connecting said outer grasping surface to said clamping inner surface, said clamping inner surface being in opposition to the clamping inner surface of the other leg member, said first leg member having a hole therein,
b) handle having a base and an actuating trigger movably attached to said base,
c) clamping jaws having a first and second opposed clamping members, said first clamping member having a first grasping means and said second clamping member having a second grasping means wherein the first and second grasping means are configured on the opposing clamping members to grasp the other surfaces of a surgical clip when compressive force is applied to the surgical clip via the clamping jaws,
d) a tubular shaft for connecting said handle to said clamping jaws,
e) a longitudinal shaft connected to said handle and positioned between said clamping jaws retaining one or more surgical clips,
f) a heating element disposed on said first clamping member for heating a surgical clip,
g) a first means for activating said heating element,
h) a second means for delivering compressive force to said first and second opposed clamping members of said clamping jaws.

8. The surgical clip applying device of claim 2 wherein said base of said handle has a contact switch disposed on the surface thereof.

9. The surgical device of claim 7 wherein said first and second means are activated by squeezing said trigger of said handle so as to cause contact between said trigger and said contact switch thereby activating said switch.

* * * * *